United States Patent [19]

Waters

[11] Patent Number: 5,146,765

[45] Date of Patent: Sep. 15, 1992

[54] DEVICE FOR EVAPORATIE COOLING OF THE NECK

[76] Inventor: William A. Waters, 3648 E. 49th St., Tulsa, Okla. 74135-3102

[21] Appl. No.: 770,484

[22] Filed: Oct. 3, 1991

Related U.S. Application Data

[63] Continuation-in-part of Ser. No. 594,164, Oct. 9, 1990, abandoned.

[51] Int. Cl.$^5$ ............................................. F25D 23/12
[52] U.S. Cl. ................................... 62/259.3; 62/531; 454/370
[58] Field of Search ................ 62/259.3, 531; 454/370

[56] References Cited

U.S. PATENT DOCUMENTS

| | | | |
|---|---|---|---|
| 2,366,989 | 1/1945 | Robertson | 62/530 |
| 3,017,888 | 1/1962 | Weiner | 62/259.3 |
| 3,029,438 | 4/1962 | Henschel | 62/259.3 |
| 3,096,702 | 7/1963 | Malone, Sr. et al. | 454/370 |
| 3,548,415 | 12/1970 | Waters | 62/259.3 |
| 4,744,106 | 5/1988 | Wang | 62/259.3 |

Primary Examiner—Ronald C. Capossela
Attorney, Agent, or Firm—Larson and Taylor

[57] ABSTRACT

An air conditioning unit for use in the cooling of persons includes a fan secured below the person's neck. A moistened foam necklace may be wrapped around the neck or a moistened foam pad otherwise positioned between the fan and the neck of the user. The fan of the air conditioning unit includes a frame, an electric motor mounted on the frame, a fan blade operably connected with the motor and rotatable by the motor for moving air, a battery or other power source operably connected with the motor for actuation thereof, and a switch operably connected between the battery or power source and the motor for controlling the actuation of the motor. Furthermore, the air conditioning unit includes a flexible element attached to the frame, the flexible element being constructed and arranged to be worn around the user's neck so that air generated by the moving fan blade moves against the neck area after being evaporatively cooled by the foam necklace or pad.

24 Claims, 3 Drawing Sheets

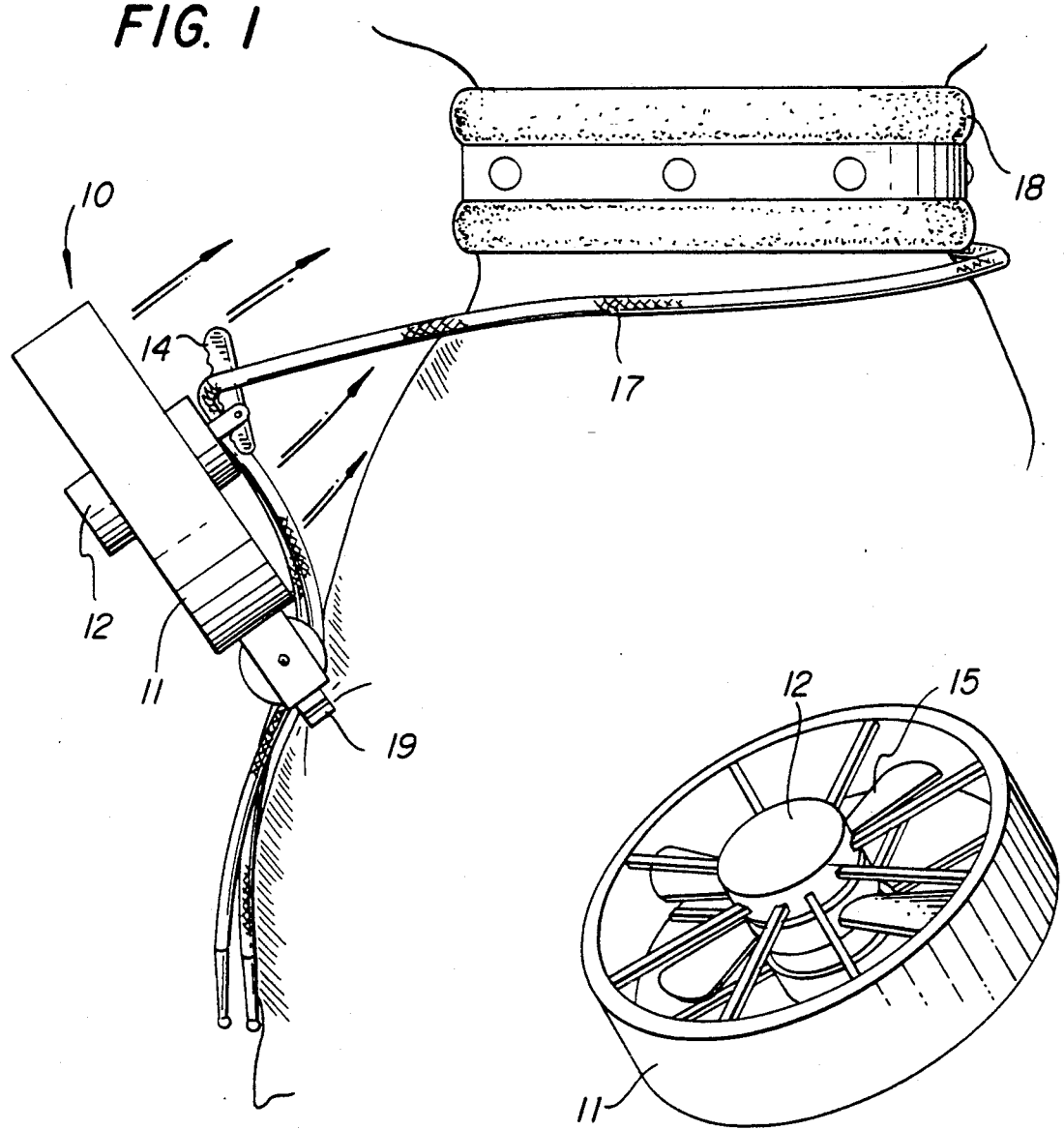
FIG. 1
FIG. 3
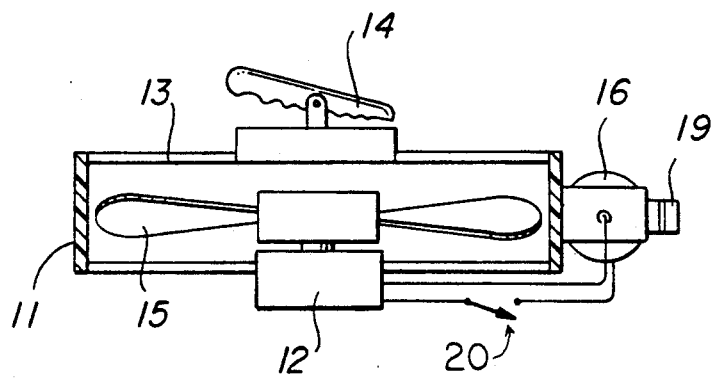
FIG. 2

DEVICE FOR EVAPORATIE COOLING OF THE NECK

This is a continuation-in-part of application Ser. No. 594,164 filed Oct. 9, 1990 now abandoned.

BACKGROUND OF THE INVENTION

This invention relates to improvements in air conditioning units for cooling persons and, more particularly, to a portable air conditioning unit to be worn in front of the neck of the user.

Persons spending a considerable amount of time in the out-of-doors, such as soldiers, athletes, sports fans, fishermen, and the like, frequently wear gear to protect themselves from the heat of the surrounding atmosphere. There is an ever-increasing demand today for providing the comfort of cooling of the wearer of such gear during hot weather conditions. Many air conditioned hats, helmets or the like, have been provided for achieving these end results, such as those shown in William A. Waters U.S. Pat. No. Re. 33,286, among others. These devices have been utilized on head gear of various types but heretofore have not been mounted on the user in other locations, which may be more convenient when persons are utilizing other types of head gear.

SUMMARY OF THE INVENTION

The present invention contemplates an air conditioning unit for use in the evaporative cooling of persons. The unit includes a fan means adapted to be secured below the person's neck and directing a moving air flow toward the person's neck. A foam necklace or pad holding moisture is positioned between the fan means and the neck of the user so that the evaporative effect will provide cooling to the wearer. The fan means of the air conditioning unit of the present invention includes a frame, an electric motor mounted on the frame, a fan blade operably connected with the motor and rotatable by it for moving air flow toward the user's neck, a battery or other electrical power providing means operably connected with the motor for actuation thereof, and a switch operably connected between the battery or other power source and the motor for controlling the actuation of the motor. Also, the air conditioning unit of the present invention contemplates the use of a flexible element attached to the frame and adapted to be worn around the user's neck to help position the fans means so that the air from the fan blade is moved against the neck area of the user.

In one embodiment, the neck of the user is encircled by a foam necklace adapted to be engaged around the user's neck and to be moistened to cooperate with the moving air flow to provide a cooling effect to the person's neck and head. Alternatively, a foam pad is positioned in front of the fan means and spaced from the neck to provide the moisture for evaporative cooling. Preferably, this foam pad is adjustably mounted, such as on the flexible element.

With the present invention, a compact and simple device is provided for cooling the neck and adjacent areas such as the head of any user.

Other features and advantages of the present invention are stated in or apparent from detailed descriptions of presently preferred embodiments of the invention found hereinbelow.

BRIEF DESCRIPTION OF THE DRAWINGS

FIG. 1 is a schematic partial view of a person's shoulders with a person utilizing one embodiment of an air conditioning unit according to the present invention.

FIG. 2 is a partial, cross-sectional view of the frame and associated elements according to the embodiment of the present invention depicted in FIG. 1.

FIG. 3 is a partial perspective view of the frame and motor according to the embodiment of the present invention depicted in FIG. 1.

FIG. 5' is an elevation view of a portion of the foam pad depicted in FIG. 5.

DESCRIPTION OF THE PREFERRED EMBODIMENTS

Figure 4:
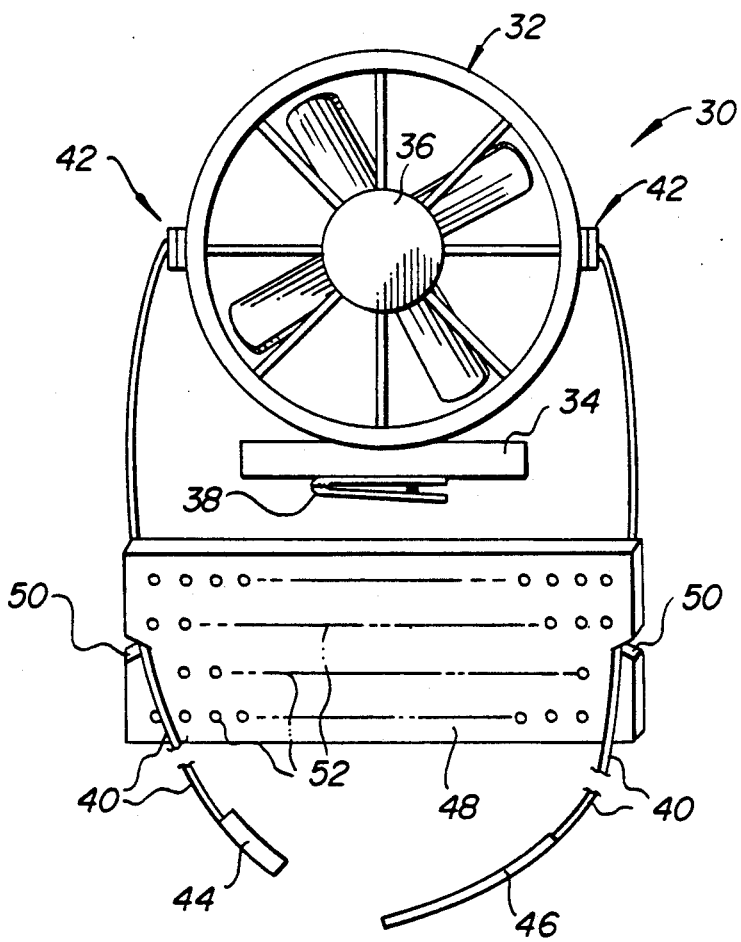
FIG. 4 is a front elevation view of a second embodiment of an air conditioning unit according to the present invention.

Referring to the drawings in detail, and particularly to FIGS. 1, 2 and 3, reference character 10 generally indicates a first embodiment of an air conditioning unit comprising a frame 11 preferably constructed from a light-weight plastic material, but not limited thereto. As shown in FIGS. 1-3, the housing or frame 11 comprises a cylindrical housing with one end supporting a motor 12 and the other end having grid 13 for protecting the air flow opening and supporting a clip means 14.

As best seen in FIG. 2, the air conditioning unit of the present invention includes electric motor 12 mounted on the frame 11. A fan blade 15 is operably connected with the shaft of the motor 12 and is rotatable thereby for moving air. A battery 16 in a housing is operably connected with the motor for actuation thereof. A switch 20 may be operably connected between the battery 16 and the motor 12 for controlling the actuation of the motor.

As best seen in FIG. 1, a flexible element 17 is adjustably attached to the frame 11 by clip means 14 and is worn around the user's neck so that the air from fan blade 15 is moved against the neck area of the wearer. As seen in FIG. 1, a foam necklace 18 is provided around the user's neck and, when moistened, aids in the evaporative cooling process caused by the moving air from the fan being directed against the foam necklace. As seen in FIG. 1, the frame 11 and its associated motor and fan blade are mounted on the flexible element at an angle so that the moving air is directed upwardly toward the underside of the user's chin. To stabilize and support the frame and motor on the user, any conventional clip 19 is secured to the battery housing. The clip 19 is attached to the user's clothing much like a tie clasp is used. Clip 19 holds air conditioning unit 10 in place on a garment of the user and thus the garment also supports most of the (small) weight of unit 10.

Whereas the invention particularly described herein includes the use of a conventional DC batteries, it is to be understood that other types of power means may be utilized in lieu thereof. For example, as shown in FIG.

8, flexible solar cells 22 may be used to generate electricity by solar energy. For convenience, solar cells 22 are mounted as a panel 24, and a clip means 26 is used to attach panel 24 to the clothes of the user at an appropriated position with wires 28 connected to motor 12. Alternately, solar cells 22 can be mounted on air conditioning unit 10, directly to the wearer, or to headwear of the user.

As an example of an embodiment of an air conditioning unit contemplated by the present invention, the motor may be a 3.0 volt light-weight motor Model RFN 30CA-11150 such as those motors on the market by Mabuchi. The fan blade may be a four-bladed, 2 1/16 inch diameter molded plastic fan from Thorgren. The batteries may be 2 AA 1½ volt batteries wired in series, or more preferable a single 3 volt battery which is lighter in weight and more compact than the two AA batteries considered. As indicated above, the frame may be of molded plastic, and in particular, may be 2 3/16 inches inside diameter. The switch may be a simple two-way switch when a simple battery power pack is utilized. Of course the size of the motor and batteries can be selected to be more heavy duty and rugged.

The flexible support for hanging the air conditioning unit around the neck is similar to the leather bolo-ties that are available on the market. The foam necklace may be made of perforated foam pads (2 inches by 5 inches) removably placed on a soft band around the neck of the wearer by velcro or similar connections with neck size adjustability using removable fasteners.

Depicted in FIG. 4 is an alternative embodiment of an air condition unit 30 according to the present invention. Unit 30 is similar to unit 10 discussed above, and includes a fan means 32 having a power source 34, motor 36, and a clip 38 to hold fan means 32 to an article of the user's clothing (typically the shirt). Attached to fan means 32 is a flexible element 40. Flexible element 40 is attached to fan means 32 by a set 42 of VELCRO tabs (one attached to an end of flexible element 40 and the other to fan means 32) so that flexible element 40 is removably attached to fan means 32. At the other ends of flexible element 40 is a set of respective VELCRO tabs 44 and 46. By use of tabs 44 and 46, and in particular how far these tabs overlap when mated together, the overall length of flexible element 40 is adjustable and hence the orientation of fan means 32 on the front of the user is also adjustable (together with clip 38).

In this embodiment of air conditioning unit 30, a foam pad 48 is provided. Foam pad 48 is mounted on flexible element 40 by use of slots 50 provided in the sides thereof. Slots 50 resiliently receive respective parts of flexible element 40 at a reduced end thereof. Therefore, it will be appreciated that foam pad 48 is removably held on flexible element 40, and additionally that foam pad 48 is manually slidable along flexible element 40 while being held thereon. As with foam necklace 18 discussed above, foam pad 40 is designed to hold moisture therein and has apertures 52 therethrough.

Figure 5:
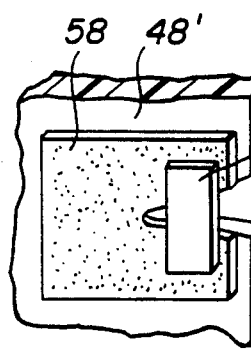
FIG. 5 is a side elevation view of a third embodiment of an air conditioning unit similar to that of FIG. 4 mounted to a user.

In use, air conditioning unit 30 is used in the manner depicted in FIG. 5 where an air conditioning unit 30' is depicted. As unit 30' is similar to unit 30, the similar elements have been identified with the same numerals to which is added a prime ('). Unit 30' differs from unit 30 in two regards. First, it will be noted that flexible element 40' does not include sets 42 of fasteners. Instead, fan means 32' is provided with studs 54 on both sides (only one of which is shown). The ends of flexible element 40' then include loops 56 (only one of which is shown) which engage the respective stud 54.

The other difference between unit 30 and unit 30' is the means for holding foam pad 48' to flexible element 40'. As shown best in FIG. 5', each slot 50' has adjacent thereto a VELCRO tab 58 with a corresponding slot. It will thus be appreciated that tab 58 serves to reinforce foam slot 50' in foam pad 48'. In addition, a mating VELCRO tab 60 is provided to engage tab 58 to cover all but the bottom or reduced end of slot 50'. Tab 60 thus serves to trap flexible element 40' in the bottom of the associated slot 50' when in place on tab 58, while still allowing flexible element 48' to be moved against friction through foam pad 48' if desired.

In use, unit 30' is mounted on the user as shown in FIG. 5. In particular, unit 30' is attached to the shirt or other regular clothes of the user by clip 38' at a location where flexible element 40' causes fan means 32' to direct air toward the neck of the user. Disposed on flexible element 40' is foam pad 48', which has been moistened. Thus, actuation of fan means 32' causes a flow of air in the direction shown by the arrows. As the air passes through or around foam pad 48', evaporative cooling of the blown air results, and this cooled air is then received by the neck and adjacent areas to cool the user. Obviously, the position and orientation of fan means 32', foam pad 48', and flexible element 40' are all adjusted for comfort and effect as desired. By making foam pad 48' removable from flexible element 40', it is possible to remoisten foam pad 48' or to supply a new moistened foam pad 48' as needed. If desired, it would also be possible to supply more than one foam pad 48' as well.

Figure 6:
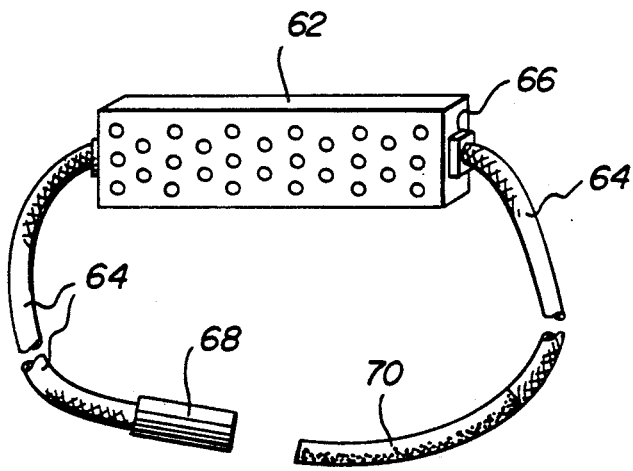
FIG. 6 is an alternative embodiment of a foam pad mounting according to the present invention.
Figure 5:
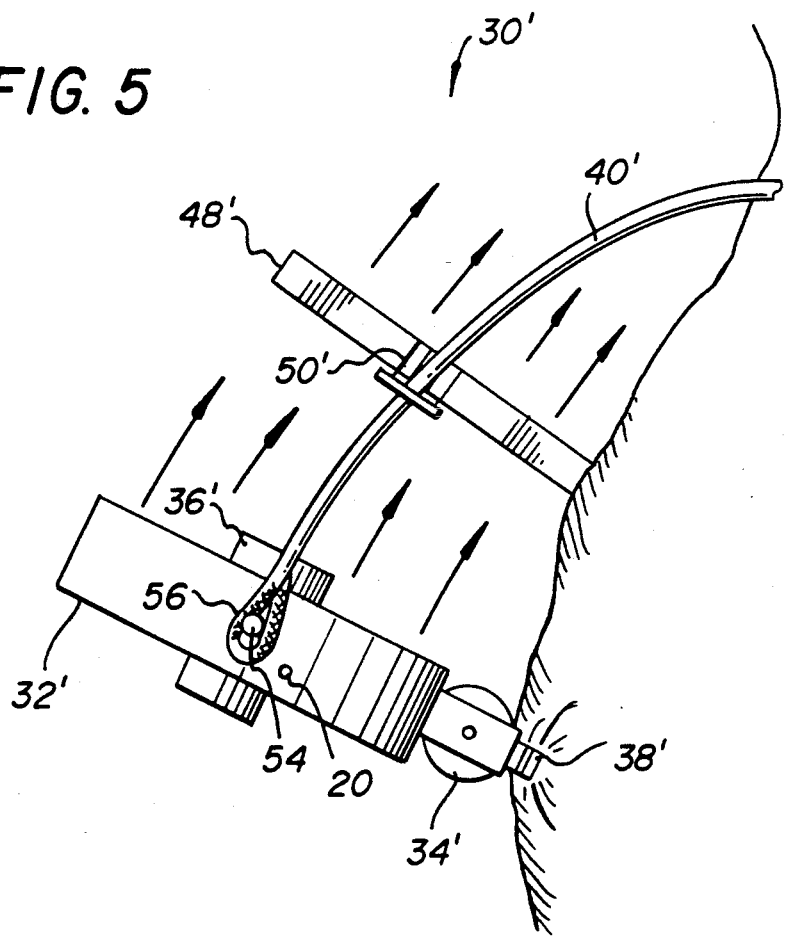

Depicted in FIG. 6 is a foam pad 62. Attached to each side of foam pad 62 is a respective end of a belt 64. Conveniently, the ends of belt 64 are removably attached by sets 66 of VELCRO tabs. Belt 64 also includes respective tabs 68 and 70 of mating VELCRO so that the overall length of belt 64 is adjustable.

In use, foam pad 62 is used, for example, in place of or in addition to foam pads 48 or 48'. Thus, it will be appreciated that foam pad 62 is used in conjunction with suitable air conditioning units according to the present invention, but that foam pad is not directly attached thereto. Instead, by suitably adjusting the length of belt 64, foam pad 62 is positioned to intercept the flow of air between the fan means and the neck of the user to provide evaporative cooling of the blown air. Because foam pad 62 is not attached to the unit or secured to the user, it is simple to lift foam pad 62 and belt 64 over the head of the user to remoisten foam pad 62 when needed.

Figure 7:
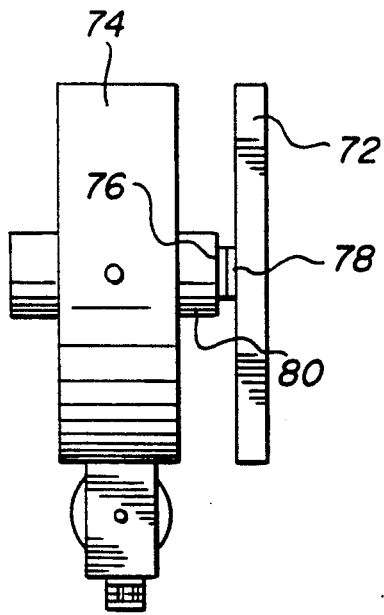
FIG. 7 is another alternative embodiment of a foam pad mounting according to the present invention.
Figure 8:
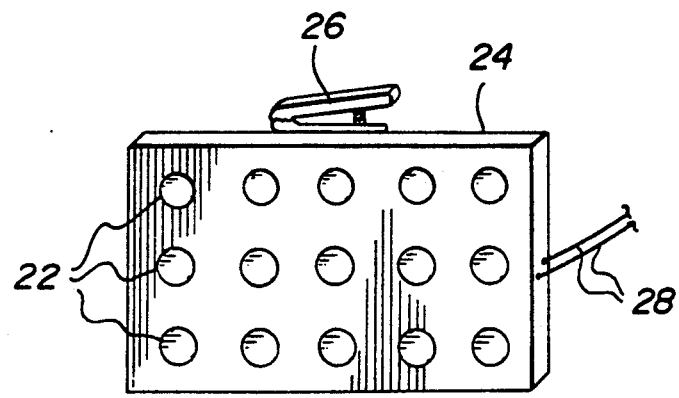
FIG. 8 is an elevation view of an alternative power source according to the present invention.

Depicted in FIG. 7 is a foam pad 72 which is mounted directly to a fan means 74 similar to fan means 32'. In this embodiment, foam pad 72 is round, and is attached directly to fan means 74. This attachment is accomplished by respective VELCRO tabs 76 and 78, which are securely attached to a central extension 80 of fan means 74 and foam pad 72, respectively. Thus, it will be appreciated that foam pad 72 is easily removable from fan means 74 when desired, and that foam pad 72 functions in the same manner as the other foam pads discussed above and can be replaced easily on fan means 74.

While various removable pads have been described above, it may be desirable to permanently mount a foam pad to a flexible element while still allowing for movement of the foam pad along the flexible element. In such a case, the flexible element can be simply threaded through suitable holes provided on respective sides of the foam pad, which holes are preferably reinforced.

Thus, whereas the present invention has been described in particular relation to the drawings attached hereto, it should be understood that other and further modifications, apart from those shown or suggested herein may be made within the spirit and scope of this invention.

What I claim is:

1. An air conditioning unit for use in the cooling of persons comprising:
    a fan means for blowing air in a direction including a) a frame, b) an electric motor mounted on said frame, c) a fan blade operably connected with said motor and rotatable thereby for moving air, d) a power source operably connected with said motor for actuation thereof, and e) a switch means operably connected between said power source and said motor for controlling the actuation of said motor;
    a flexible element attached to said fan means and adapted to be worn around a back of a user's neck so as to suspend said frame in a position whereby the direction of the air moved by said fan means is against the neck area; and
    a foam pad positioned in front of the user's neck which is moistened to cooperate with said moving air to provide evaporatively cooled air blown by said fan means to the user's neck and head, said foam pad including a mounting means for adjustably mounting said foam pad to said flexible element between said fan means and the user's neck.

2. The invention of claim 1 further comprising a clip means on said unit to clip the frame in place on a user's clothing.

3. The invention of claim 1 wherein said power source in a D.C. battery.

4. The invention of claim 1 wherein said power source is a plurality of solar cells.

5. The invention of claim 1 and further including a clip means mounted on the frame for adjustably mounting said flexible element to said frame.

6. The invention of claim 1 wherein said mounting means includes a slot on respective sides of said foam pad in which respective portions of said flexible element are resiliently received.

7. The invention of claim 1 wherein said mounting means includes a slot on respective sides of said foam pad in which respective portions of said flexible element are received and a respective holding means for releasably holding said respective portions of said flexible element in associated said slots.

8. The invention of claim 1 wherein said foam pad includes a series of apertures therein through which the air blown by said fans means directly passes.

9. The invention of claim 1 and further comprising a clip means on said unit to clip said fan means in place on a user's clothing.

10. The invention of claim 9 wherein said foam pad includes a series of apertures therein through which the air blown by said fans means directly passes.

11. An air conditioning unit for use in the cooling of persons comprising:
    a fan means for blowing air in a direction including a) a frame, b) an electric motor mounted on said frame, c) a fan blade operably connected with said motor and rotatable thereby for moving air, d) a power source operably connected with said motor for actuation thereof, and e) a switch means operably connected between said power source and said motor for controlling the actuation of said motor;
    a flexible element attached to said fan means and adapted to be worn around a back of a user's neck so as to suspend said frame in a position whereby the direction of the air moved by said fan means is against the neck area; and
    a foam pad positioned in front of the user's neck which is moistened to cooperate with said moving air to provide evaporatively cooled air blown by said fan means to the user's neck and head, said foam pad including a second flexible element to which said foam pad is attached whereby said second flexible element is worn around a back of the neck of the user to adjustably mount said foam pad between said fan means and the user's neck.

12. The invention of claim 11 further comprising a clip means on said unit to clip the frame in place on a user's clothing.

13. The invention of claim 11 wherein said power source is a D.C. battery.

14. The invention of claim 11 wherein said power source is a plurality of solar cells.

15. The invention of claim 11 and further including a clip means mounted on the frame for adjustably mounting said flexible element to said frame.

16. The invention of claim 11 wherein said foam pad includes a series of apertures therein through which the air blown by said fans means directly passes.

17. The invention of claim 11 and further comprising a clip means on said unit to clip said fan means in place on a user's clothing.

18. An air conditioning unit for use in the cooling of persons comprising:
    a fan means for blowing air in a direction including a) a frame, b) an electric motor mounted on said frame, c) a fan blade operably connected with said motor and rotatable thereby for moving air, d) a power source operably connected with said motor for actuation thereof, and e) a switch means operably connected between said power source and said motor for controlling the actuation of said motor;
    a flexible element attached to said fan means and adapted to be worn around a back of a user'neck so as to suspend said frame in a position whereby the direction of the air moved by said fan means is against the neck area; and
    a foam pad positioned in front of the user's neck which is moistened to cooperate with said moving air to provide evaporatively cooled air blown by said fan means to the user's neck and head, said foam pad including a mounting means for adjustably mounting said foam pad to said fan means between said fan means and the user's neck.

19. The invention of claim 18 further comprising a clip means on said unit to clip the frame in place on a user's clothing.

20. The invention of claim 18 wherein said power source is a D.C. battery.

21. The invention of claim 18 wherein said power source is a plurality of solar cells.

22. The invention of claim 18 and further including a clip means mounted on the frame for adjustably mounting said flexible element to said frame.

23. The invention of claim 18 wherein said foam pad includes a series of apertures therein through which the air blown by said fans means directly passes.

24. The invention of claim 18 and further comprising a clip means on said unit to clip said fan means in place on a user's clothing.

* * * * *

UNITED STATES PATENT AND TRADEMARK OFFICE
CERTIFICATE OF CORRECTION

PATENT NO. : 5,146,765
DATED : 09/15/92
INVENTOR(S) : William A. Waters

It is certified that error appears in the above-identified patent and that said Letters Patent is hereby corrected as shown below:

On the cover page, in the title of the invention "EVAPORATIE" to read
--EVAPORATIVE--

Column 1, in the title of the invention "EVAPORATIE" should read
--EVAPORATIVE--

Column 1, line 50, "fans means" should read --fan means--

Column 6, line 42, "user'neck" should read --user's neck--

Signed and Sealed this

Fifth Day of October, 1993

*Attest:*

BRUCE LEHMAN

*Attesting Officer*     *Commissioner of Patents and Trademarks*